(12) United States Patent
Macy, Jr.

(10) Patent No.: US 11,305,100 B2
(45) Date of Patent: *Apr. 19, 2022

(54) APPARATUSES AND METHODS FOR MEDICATION ADMINISTRATION

(71) Applicant: Hospi Corporation, Concord, CA (US)

(72) Inventor: Bradford Macy, Jr., Concord, CA (US)

(73) Assignee: Hospi Corporation, Concord, CA (US)

( * ) Notice: Subject to any disclaimer, the term of this patent is extended or adjusted under 35 U.S.C. 154(b) by 306 days.

This patent is subject to a terminal disclaimer.

(21) Appl. No.: 14/074,613

(22) Filed: Nov. 7, 2013

(65) Prior Publication Data

US 2014/0066848 A1 Mar. 6, 2014

Related U.S. Application Data

(63) Continuation of application No. 12/235,601, filed on Sep. 23, 2008, now Pat. No. 8,603,029.

(Continued)

(51) Int. Cl.
*A61M 31/00* (2006.01)
*A61M 25/00* (2006.01)
(Continued)

(52) U.S. Cl.
CPC ........ *A61M 31/007* (2013.01); *A61M 25/007* (2013.01); *A61M 25/0068* (2013.01);
(Continued)

(58) Field of Classification Search
CPC .. A61M 2025/0008; A61M 2025/0037; A61M 25/0068; A61M 25/007;
(Continued)

(56) References Cited

U.S. PATENT DOCUMENTS 3,409,015 A * 11/1968 Swanson ........... A61M 25/1018
604/99.03
3,416,567 A 12/1968 von Dardel et al.
(Continued)

FOREIGN PATENT DOCUMENTS

DE 202008009245 U1 10/2008
EP 2075032 A1 7/2009
(Continued)

OTHER PUBLICATIONS

Dictionary.com. "distend". Accessed at https://www.dictionary.com/browse/distend?s=t. Accessed on Sep. 28, 2019 (Year: 2019).*
(Continued)

*Primary Examiner* — Bhisma Mehta
*Assistant Examiner* — Larry R. Wilson
(74) *Attorney, Agent, or Firm* — Shay Glenn LLP

(57) ABSTRACT

A rectal medication administration device includes a tube, a balloon, a first valved port, and a second valved port. The tube includes a first lumen, a second lumen, and a plurality of holes extending from the first lumen therethrough. The balloon is proximal to the holes, is in communication with the second lumen, and is configured to be inflated to hold the tube in place within a patient's rectum. The first valved port is in communication with the first lumen and opens when connected to a first syringe or infusion set to provide medication transmission therethrough and closes when the first syringe or infusion set is withdrawn. The second valved port is in communication with the second lumen and opens when connected with a second syringe or infusion set to provide fluid to inflate the balloon and closes when the second syringe or infusion set is withdrawn.

18 Claims, 4 Drawing Sheets

Related U.S. Application Data

(60) Provisional application No. 60/998,286, filed on Oct. 10, 2007.

(51) Int. Cl.
 *A61M 25/04* (2006.01)
 *A61M 25/02* (2006.01)
 *A61M 25/10* (2013.01)

(52) U.S. Cl.
 CPC ............ *A61M 25/02* (2013.01); *A61M 25/04* (2013.01); *A61M 31/00* (2013.01); *A61M 25/10* (2013.01); *A61M 2025/0008* (2013.01); *A61M 2025/0037* (2013.01); *A61M 2210/1067* (2013.01)

(58) Field of Classification Search
 CPC ...... A61M 25/04; A61M 25/10; A61M 39/26; A61M 2210/1067; A61M 25/02; A61M 31/00; A61M 31/007; A61M 2210/1064; A61M 25/0075; A61M 25/1018–10183; A61M 25/10185–10186
 See application file for complete search history.

(56) References Cited

U.S. PATENT DOCUMENTS

| | | | |
|---|---|---|---|
| 3,509,884 A * | 5/1970 | Bell | A61M 25/04 604/101.05 |
| 3,926,705 A * | 12/1975 | Todd | A61M 25/0015 156/155 |
| 4,119,098 A | 10/1978 | Bolduc et al. | |
| 4,403,982 A | 9/1983 | Clayton | |
| 4,516,578 A | 5/1985 | Shuffield | |
| 4,535,820 A | 8/1985 | Raines | |
| 4,946,448 A | 8/1990 | Richmond | |
| 4,966,199 A | 10/1990 | Ruschke | |
| 5,098,405 A | 3/1992 | Peterson et al. | |
| 5,197,950 A * | 3/1993 | Clayton | A61M 3/0295 604/262 |
| 5,312,343 A | 5/1994 | Krog et al. | |
| 5,509,929 A | 4/1996 | Hascoet et al. | |
| 5,830,186 A * | 11/1998 | Gonzales | A61M 31/00 604/131 |
| 5,843,723 A | 12/1998 | Dubensky, Jr. et al. | |
| 5,846,216 A | 12/1998 | Gonzales et al. | |
| 5,910,128 A | 6/1999 | Quinn | |
| 6,077,243 A | 6/2000 | Quinn | |
| 6,102,929 A | 8/2000 | Conway et al. | |
| 6,165,168 A | 12/2000 | Russo | |
| 6,254,570 B1 * | 7/2001 | Rutner | A61M 25/0017 604/101.01 |
| 6,468,245 B2 | 10/2002 | Alexandersen | |
| 6,569,132 B1 | 5/2003 | Dvärsäter | |
| 6,623,453 B1 | 9/2003 | Guibert et al. | |
| 6,652,441 B2 | 11/2003 | Weinberger et al. | |
| 7,022,105 B1 | 4/2006 | Edwards | |
| 7,387,638 B2 | 6/2008 | Gonzales | |
| 8,529,543 B2 | 9/2013 | Macy, Jr. | |
| 8,603,029 B2 | 12/2013 | Macy, Jr. | |
| 2002/0082547 A1 * | 6/2002 | Deniega | A61M 25/0043 604/48 |
| 2003/0060799 A1 | 3/2003 | Arenberg et al. | |
| 2003/0153897 A1 | 8/2003 | Russo | |
| 2004/0039348 A1 * | 2/2004 | Kim | A61M 3/0241 604/264 |
| 2004/0124389 A1 * | 7/2004 | Phillips | A61M 39/02 251/149.4 |
| 2004/0236365 A1 | 11/2004 | Cioanta et al. | |
| 2005/0054996 A1 | 3/2005 | Gregory | |
| 2005/0267415 A1 | 12/2005 | Jacques | |
| 2006/0178645 A1 | 8/2006 | Peppel | |
| 2006/0276746 A1 | 12/2006 | Burnside et al. | |
| 2007/0073216 A1 | 3/2007 | McAuliffe et al. | |
| 2009/0205658 A1 | 8/2009 | Tanaka et al. | |
| 2009/0232586 A1 | 9/2009 | Diodati et al. | |
| 2009/0259175 A1 | 10/2009 | Nordgren | |
| 2010/0121309 A1 | 5/2010 | Macy, Jr. | |

FOREIGN PATENT DOCUMENTS

| | | |
|---|---|---|
| EP | 2140907 A1 | 1/2010 |
| WO | WO 03/018105 A1 | 3/2003 |
| WO | WO2007/120620 A2 | 10/2007 |

OTHER PUBLICATIONS

The Editors of Encyclopaedia Britannica. "Defecation". Encyclopaedia Britannica, Inc. https://www.britannica.com/science/defecation-physiology. Published Nov. 6, 2017. Accessed Sep. 28, 2019. (Year: 2019).*

Macy et al.; U.S. Appl. No. 14/372,906 entitled "Valved enteral administration assembly," filed Jul. 17, 2014.

Bard Corp.; Colon/Rectal Tubs (product list); downloaded from http://www.bardmedical.com/products/loadproduct.aspx?prodID=340 on May 10, 2010; 2 pgs.

* cited by examiner

APPARATUSES AND METHODS FOR MEDICATION ADMINISTRATION

CROSS REFERENCE TO RELATED APPLICATIONS

This application is a continuation of U.S. patent application Ser. No. 12/235,601, filed Sep. 23, 2008, titled "APPARATUSES AND METHODS FOR MEDICATION ADMINISTRATION," now U.S. Patent Application Publication No. US-2009-0099546-A1, which claims priority to U.S. Provisional Patent Application No. 60/998,286, filed Oct. 10, 2007 and titled "RECTAL MEDICATION ADMINISTRATION TUBE," each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

At least some embodiments of the disclosure relate to delivery of medications in general and, more particularly but not limited to, delivery of medication into rectum.

BACKGROUND

Most patients lose the ability to swallow at a certain point near death, during which symptom management can become challenging, as symptoms, such as pain, shortness of breath, restlessness or agitation, tend to worsen.

The rectum is a good alternative for hospice patients when the oral route fails. The walls of the rectum absorb many medications fast and effectively.

Traditional forms of rectal administration use suppositories and/or gels that are injected using a pre-filled syringe. These traditional approaches typically involve moving or repositioning the patient, which is many times uncomfortable and invasive for the patient and difficult for the caregivers. Such a process can be painful, especially if the patient has hemorrhoids.

SUMMARY OF THE DISCLOSURE

Apparatuses and methods for medication administration via a body cavity are described herein. Some embodiments are summarized in this section.

In one aspect, a medication administration device includes: a tip portion having a plurality of holes and a balloon defining a balloon cavity. When the balloon is deflated the tip portion can be inserted into a body cavity, such as the rectum, to allow medication delivery through the holes in the tip portion. The balloon is configured to prevent the tip portion from being withdrawn from the body cavity and, in at least some embodiments, to hold medication within the rectum after the balloon is inflated inside the body cavity. The device further includes a port portion that has a first port and a second port, and an elongated tubular portion that is coupled between the tip portion and the port portion. The tubular portion has a first lumen and a second lumen. The first lumen connects the first port to the plurality of holes in the tip portion; and the second lumen connects the second port to the balloon cavity.

In one embodiment, the tip portion is configured to be inserted into rectum; the diameter of the first lumen connecting the first port to the plurality of holes is no more than 3 millimeters to limit a volume of the first lumen; and the volume of the first lumen is no more than 4 milliliter to reduce medication dilution after medication is flushed out of the first lumen into the body cavity through the holes in the tip portion.

In one embodiment, the elongated tubular portion is sufficient to connect the port portion to a front of portion of a patient while the tip portion is engaged within the rectum of the patient.

In one embodiment, the holes are configured to allow a limited amount of medication to be evenly distributed to an area of the rectum when medication is pressured through the first lumen via the first port.

In one embodiment, the tip of the tip portion is closed.

In one embodiment, when the balloon engages rectal sphincter, the holes in the tip portion are positioned at a distal portion of the rectum.

In one embodiment, the outer diameter of the tubular portion is between 5.5 to 7 millimeters; the diameter of the first lumen is 3 millimeters; a diameter of the second lumen is less than 1 millimeter; a distance between a tip of the tip portion and a center of the balloon is between 2.5 to 3.5 inches; a diameter of the holes is between 1.5 to 2 millimeters; and spacing between the holes is between 4 to 6 millimeters.

In one embodiment, the first and second ports are configured to interface with a syringe. The first and second ports are configured to close when syringes are withdrawn from the first and second ports. For example, each of the first and second ports may include a lock connector and valve.

In another aspect, a medication administration device includes: a tip portion having a plurality of holes and a balloon defining a balloon cavity. When the balloon is deflated the tip portion can be inserted into the rectum to allow medication delivery through the holes in the tip portion. The balloon is configured to prevent the tip portion from being withdrawn from the rectum after the balloon is inflated inside the rectum. The holes are distributed in the tip portion to deliver medication in a solution form or a suspension form to a distal portion of the rectum. The medication administration device further includes a port portion that has a first port and a second port. Each of the first and second port has a Luer lock connector with a valve, where the valve opens when a common Luer lock syringe is inserted and closes when the syringe is withdrawn. The medication administration device further includes an elongated tubular portion coupled between the tip portion and the port portion. The tubular portion has a first lumen and a second lumen, where the first lumen connects the first port to the plurality of holes in the tip portion, and the second lumen connects the second port to the balloon cavity.

In a further aspect, a method includes: providing a device having a tip portion, a port portion and an elongated tubular portion coupled between the tip portion and the port portion. The tip portion has a plurality of holes and a balloon. The port portion has a first port connected by a first lumen in the tubular portion to the holes in the tip portion, and a second port connected by a second lumen in the tubular portion to the tip portion to inflate or deflate the balloon. The method further includes: inserting the tip portion of the device into the rectum of a patient while the balloon is deflated; inserting a first syringe into the second port to inject a predetermined amount of water into the balloon to inflate the balloon; removing the first syringe from the second port; inserting a second syringe into the first port to inject medication in a liquid form or a suspension form into the first lumen for dissemination in a distal portion of the rectum; and removing the second syringe from the first port until a next scheduled medication time.

In one embodiment, the method further includes: injecting a predetermined amount of water into the first lumen to flush medications from the first lumen into the distal portion of the rectum; inserting an empty syringe into the second port to remove water from the balloon to deflate the balloon; and removing the tip portion of the device from the rectum after the balloon is deflated.

In one embodiment, the method further includes periodically disseminating medication to the distal portion of the rectum through the first port without removing the tip portion of the device from the rectum.

Other features will be apparent from the accompanying drawings and from the detailed description which follows.

BRIEF DESCRIPTION OF THE DRAWINGS

The embodiments are illustrated by way of example and not limitation in the figures of the accompanying drawings in which like references indicate similar elements.

DETAILED DESCRIPTION

The following description and drawings are illustrative and are not to be construed as limiting. Numerous specific details are described to provide a thorough understanding. However, in certain instances, well known or conventional details are not described in order to avoid obscuring the description. References to one or an embodiment in the disclosure are not necessarily references to the same embodiment; and, such references mean at least one.

One embodiment of the disclosure provides a device for medication administration, which allows for comfortable administration of medication in a liquid form. The medication could be either in solution, such as intravenous preparations, or in suspension, such as medications which are crushed and added with water, or another solvent or liquid.

Although some embodiments are described in the context of rectal medication administration, the devices can also be used in other applications.

In one embodiment, a device for rectal medication administration includes a medication administration port connected to a tube to carry the medication into the rectum. There are a number of small holes at the end of the tube to disperse the medication onto the rectal mucosa.

In one embodiment, the end of the tube is ballooned, which when inflated in the rectum holds the end of the tube in the rectum for ongoing medication administration. For example, since the end of the tube is held in place, medication can be given intermittently or continuously on an ongoing basis. In one embodiment, the medication administration port closes automatically when the syringe is removed, allowing for medications to be given intermittently. The medication port can also be used for continuous infusion. For example, intravenous tubing can be attached to the medication administration port for a continuous infusion rectally.

Alternatively, the end of the tube is not ballooned; and the device can be configured for single use.

Figure 1:
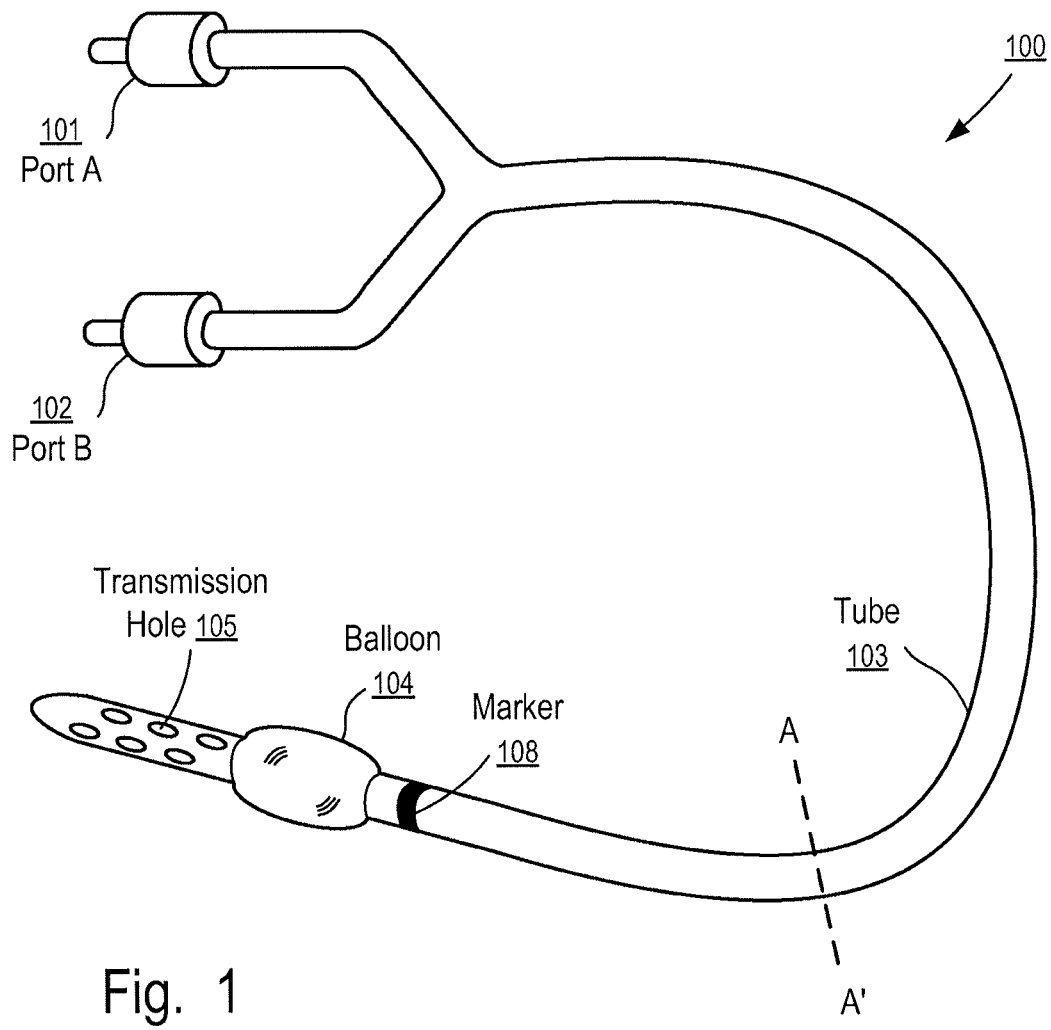
FIG. 1 shows a device for medication administration according to one embodiment.

FIG. 1 shows a device for medication administration according to one embodiment. The device 100 illustrated in FIG. 1 can be used for administering medications into rectum.

In FIG. 1, the device 100 has a hollow tube 103. In one embodiment, the tube 103 is about 15-17 inches long with a diameter of 18 French (6 mm), but it may have different sizes in different embodiments. The tube 103 may be made of any of several different soft, flexible, bio-safe materials, for example, latex, silicone, or soft plastic. The tube 103 provides a path for the medication to travel from a medication administration port 102 to the tip portion of the tube 103.

In one embodiment, the tip portion of the tube 103 is to be placed in the rectum of the patient, human or other animal. The tip portion of the tube 103 has two holes for the medicine to pass into the rectum in one embodiment, but have more holes in other embodiments.

In FIG. 1, the tip portion of the tube 103 includes a balloon 104 and an optional marker 108 which is a guide for depth of placement of the tip portion of the tube 103 (e.g., for placement in rectum).

In one embodiment, the marker 108 is a black line 3 inches way from the end of the tube. In other embodiments, the marker 108 may be 3 to 4.5 inches way from the end of the tube. The marker 108 can be placed at a location based on the desired length of the tip portion that is to be inserted into the rectum.

In one embodiment, the tube is long enough to allow the medication administration port to be brought around to the front of a human patient, either between the legs, or around the buttocks, allowing access to the port without moving the patient, although this may not be the only reason or use for the length of the tube.

The tip portion of the device illustrated in FIG. 1 may be left in the rectum for an indefinite period of time to allow ongoing medication administration without the discomfort of having to pass through the rectal sphincter with each dose. The tube stays in place by inflation of a balloon 104 on the inside of the rectum, just past the rectal sphincter in most cases.

In one embodiment the balloon has a 10 milliliters capacity, but may have more or less capacity, or may not be present at all in some embodiments. In one embodiment, when fully inflated, the balloon has a diameter approximately one inch.

The balloon can be made of a material which is pliable enough to pass through the rectal sphincter with ease should defecation occur. In this case, the balloon could be deflated, the tube reinserted and the balloon re-inflated.

The device 100 illustrated in FIG. 1 has a balloon inflation port 101 which opens when a syringe is attached and closes when removed, which allows the balloon to be inflated and deflated as needed, for instance, if the patient needed to defecate or the tube was no longer needed. The balloon can be inflated by injecting the volume of liquid needed into the port 101. This fluid travels through a balloon inflation lumen 107 (illustrated in FIG. 2) inside the tube 107, which runs along side the medication lumen 106 (illustrated in FIG. 2).

The technology for both the balloons and ports are in existence in many forms and are extensively used in human and veterinary medicine today.

Figure 2:
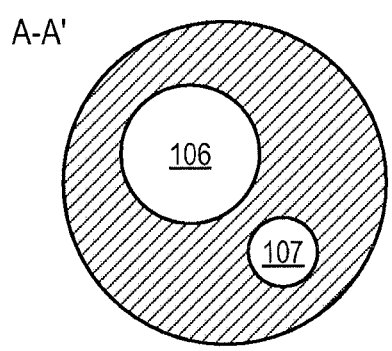
FIG. 2 shows a cross section of the device illustrated in FIG. 1.

FIG. 2 shows a cross section A-A' of the device illustrated in FIG. 1. The cross section A-A' illustrated in FIG. 2 is substantially perpendicular to the longitudinal axis of the tube 103. The cross section A-A' of the device shows the medication lumen 106, separate from the balloon inflation lumen 107. The medication lumen 106 provides a path for medications to travel from the medication port 102 to the holes 105 in the tip portion of the tube 103. The balloon inflation lumen 107 provides a path for balloon inflation liquid, such as water, to travel from the balloon inflation port 101 into the cavity of the balloon 104.

Figure 3:
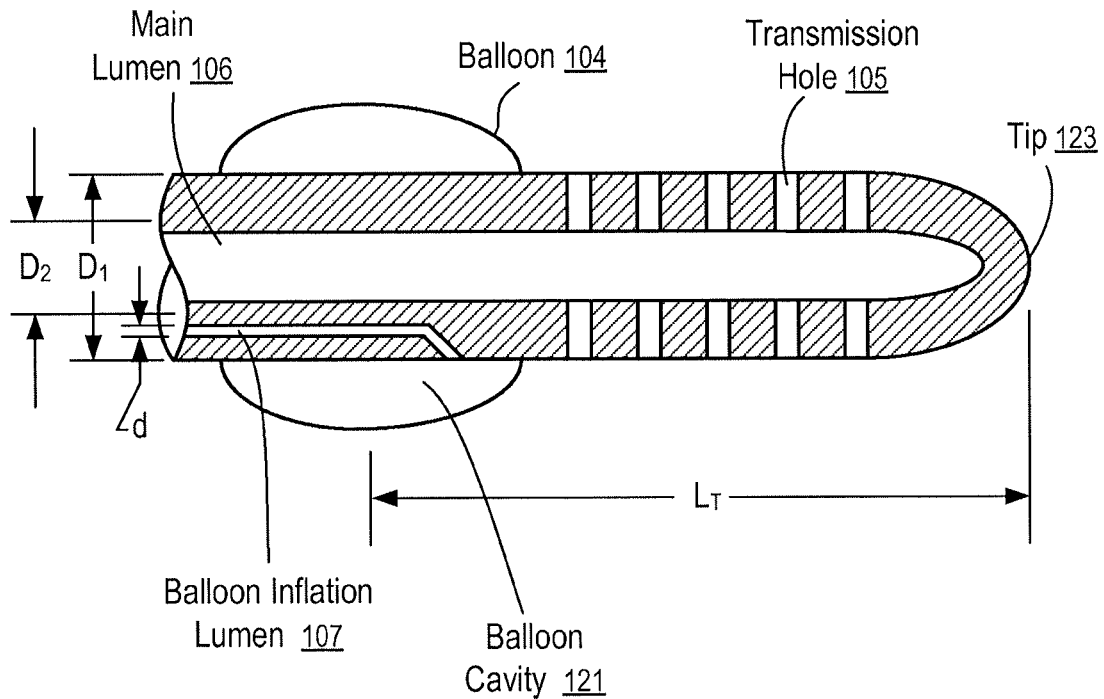
FIG. 3 shows a cross section of a tip portion of the device illustrated in FIG. 1.

FIG. 3 shows a cross section of a tip portion of the device 100 illustrated in FIG. 1. The cross section illustrated in FIG. 3 is substantially along the longitudinal axis of the tube 103.

In one embodiment, the tip 123 of the device 100 is closed, as illustrated in FIG. 3. Alternatively, the tip 123 of the device 100 may also have one or more small holes (e.g., a hole having a diameter smaller than the diameter $D_2$ of the main, medication lumen 106). Alternatively, the tip 123 of the device 100 may be open (e.g., with a hole having a diameter substantially the same as the diameter $D_2$ of the main, medication lumen 106). However, tips that are partially or completely open may be clogged by stool and/or may cause discomfort to the patient during insertion.

In FIG. 3, the balloon inflation lumen 107 connects to the balloon cavity 121. The balloon 104 is inflated when a balloon inflation liquid, such as water, is injected into the balloon cavity via the balloon inflation lumen 107 (and via the balloon inflation port 101). The balloon 104 is inflated by the water injected into a cavity separate from the medication lumen 106 of the tube 103 through which the medication travels.

In one embodiment, the tip portion of the device 100 has a multiplicity of transmission holes 105, which allow a specific injected amount of liquid, carrying the medication, to be distributed to as large a surface in the distal rectum as possible (without having to fill up the rectum). In some embodiments, the transmission holes 105 are configured to have a pattern and/or orientation to target the application of the medication to a specific area to which the holes are pointing to.

In one embodiment, to apply the medication to a distal ⅓ portion of rectum, the tip portion has a length $L_T$ between 2.5 to 3.5 inches from the tip 123 to the center of the balloon.

In one embodiment, the diameter d of the balloon inflation lumen is about 1 millimeter; and the diameter $D_2$ of the main, medication lumen 106 is no more than 3 millimeters (e.g., having a diameter of 2 millimeters) to limit the volume of medication lumen. In one embodiment, the volume of the medication lumen is less than 4 milliliters (e.g., 3 milliliters) to limit the amount of dilution caused by flushing the medication out of the medication lumen 106 and into the patient.

For example, after the medication is injected into the medication port 102, a portion of the medication remains in the medication lumen 106. A predetermined amount of water, preferably equal to the volume of the medication lumen 106 can be injected into the medication port 102 to flush the medication out of the medication lumen 106. The water stays in the medication lumen 106 would dilute the medication applied at the next medication time. Thus, limiting the volume of the medication lumen 106 can limit the dilution caused by the water used to flush the medication out of the medication lumen 106 and into the patient. Secondly, limiting the overall flush volume reduces discomfort caused by large volumes of liquid stimulating the rectal smooth muscle.

In one embodiment, the outer diameter $D_1$ of the tube is between 5.5 to 7 millimeters (e.g., 6 millimeters).

In one embodiment, the diameter of the transmission holes 105 is between 1.5 to 2 millimeters; and spacing between the holes is between 4 to 6 millimeters (e.g., 5 millimeters)

Figure 4:
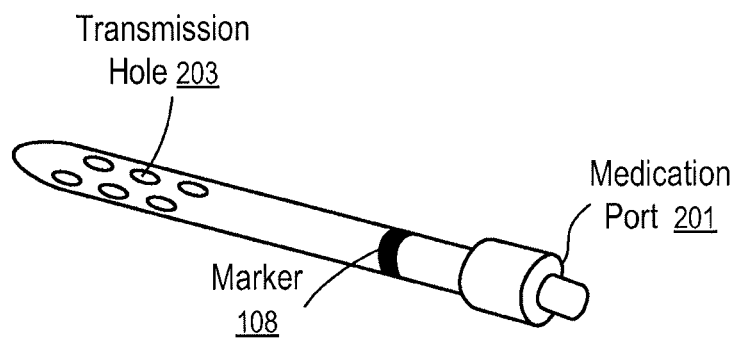
FIG. 4 shows an alternative device according to one embodiment.

FIG. 4 shows an alternative device according to one embodiment. The device illustrated in FIG. 4 does not have a balloon. The optional marker 108 is used as a guide of placement. The device has a medication port 201, which connects to the transmission holes 203 by a lumen in the device running from the port 201.

The device can be configured as a single use device. The device illustrated in FIG. 4 allows for administration of medication without leaving the tip portion of the device in the rectum. The use of less material makes the device illustrated in FIG. 4 more cost effective if it is not necessary to keep the tip portion of the device in rectum for periodic medications, or for continuous infusion.

In one embodiment, the device as illustrated in FIG. 4 is four inches long and 16 Frenches in diameter, but may be other lengths or diameters in other embodiments. The material it is made of would be stiff enough to insert into the rectum without bending on itself, but pliable enough that it could not penetrate the rectal wall.

In one embodiment, a line marked around the entire diameter of the tube is about 2.5 to 3 inches from the tip, to indicate the depth of insertion into the rectum, but this may or may not be present in other embodiments.

When the device illustrated in FIG. 4 is used, medication can be administered through the self closing port 201, which is similar to the port 101 of the device 100 illustrated in FIG. 1. The medication can be given via syringe in most cases, but could be any device with a standard syringe tip or Luer lock tip. The medication travels through the tube, into the rectum, and is released in the rectum through small holes 203 in the last inch of the tube 203.

In one embodiment, the diameter of the inner lumen of the tube is 1.5 millimeters, leaving a very small amount of medication in the lumen of the tube after administration, thus avoiding the need to flush the device after medication administration in most cases.

Alternatively, the tip portion that has the transmission holes 203 may be left in the rectum for a period of time for ongoing medications.

Figure 5:
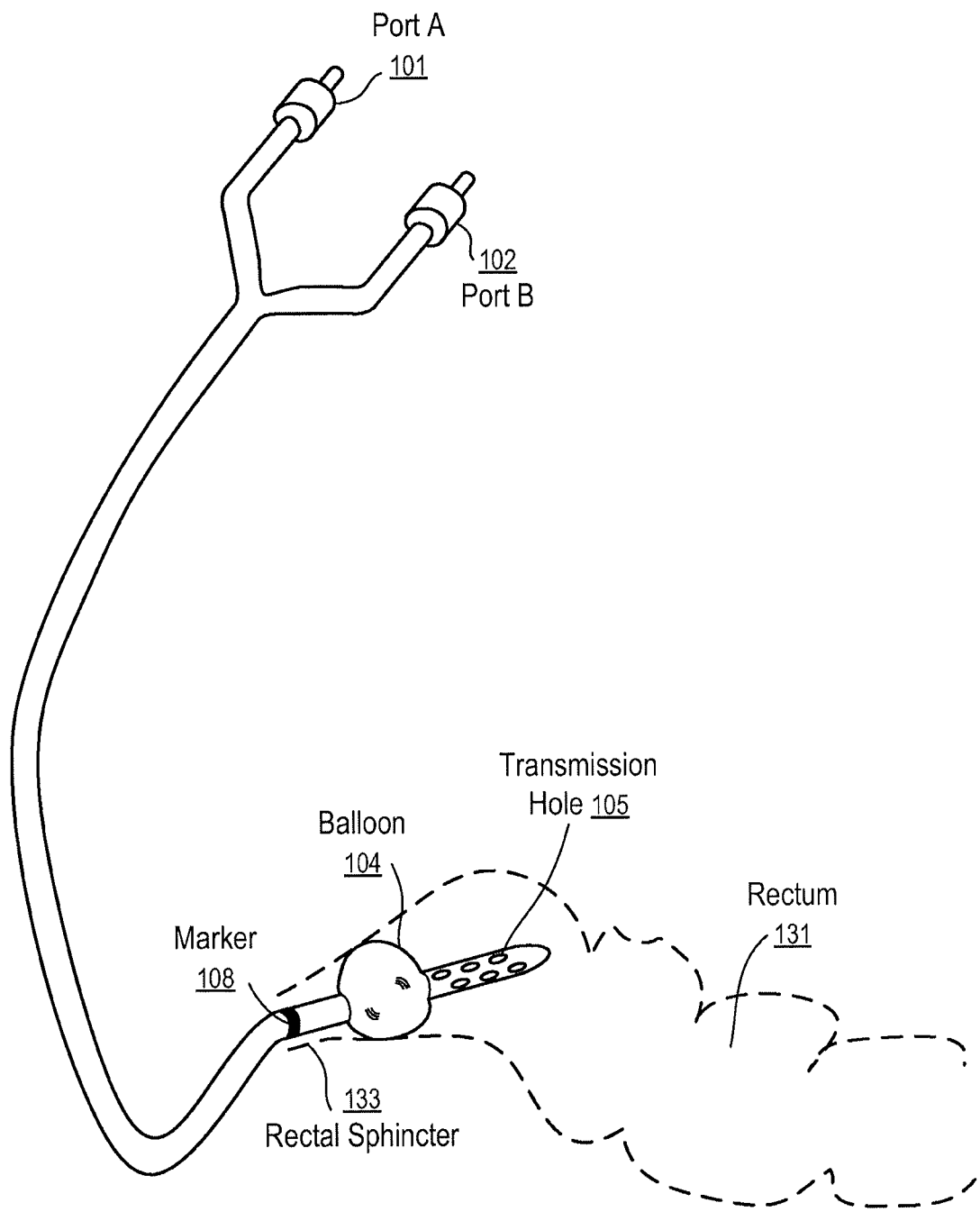
FIG. 5 illustrates the use of a device for medication administration in rectum according to one embodiment.

FIG. 5 illustrates the use of a device for medication administration in rectum. In FIG. 5, the balloon 104 is inflated to keep the tip portion of the device 100 in the rectum 131, after the tip portion is inserted passed the rectal sphincter 133. The device 100 has a length sufficient long to allow the ports 101 and 102 be brought to a convenient location for medication administration, while the patient can be in a comfortable position to receive medication. Thus, repeated application of medication would be less intrusive, less discomfort for the patient and would be easier for the caregivers.

As illustrated in FIG. 5, the transmission holes 105 in the tip portion of the device 100 allow the application of the medication to be targeted at a specific portion of the rectum 131 (e.g., a distal portion of the rectum).

Figure 6:
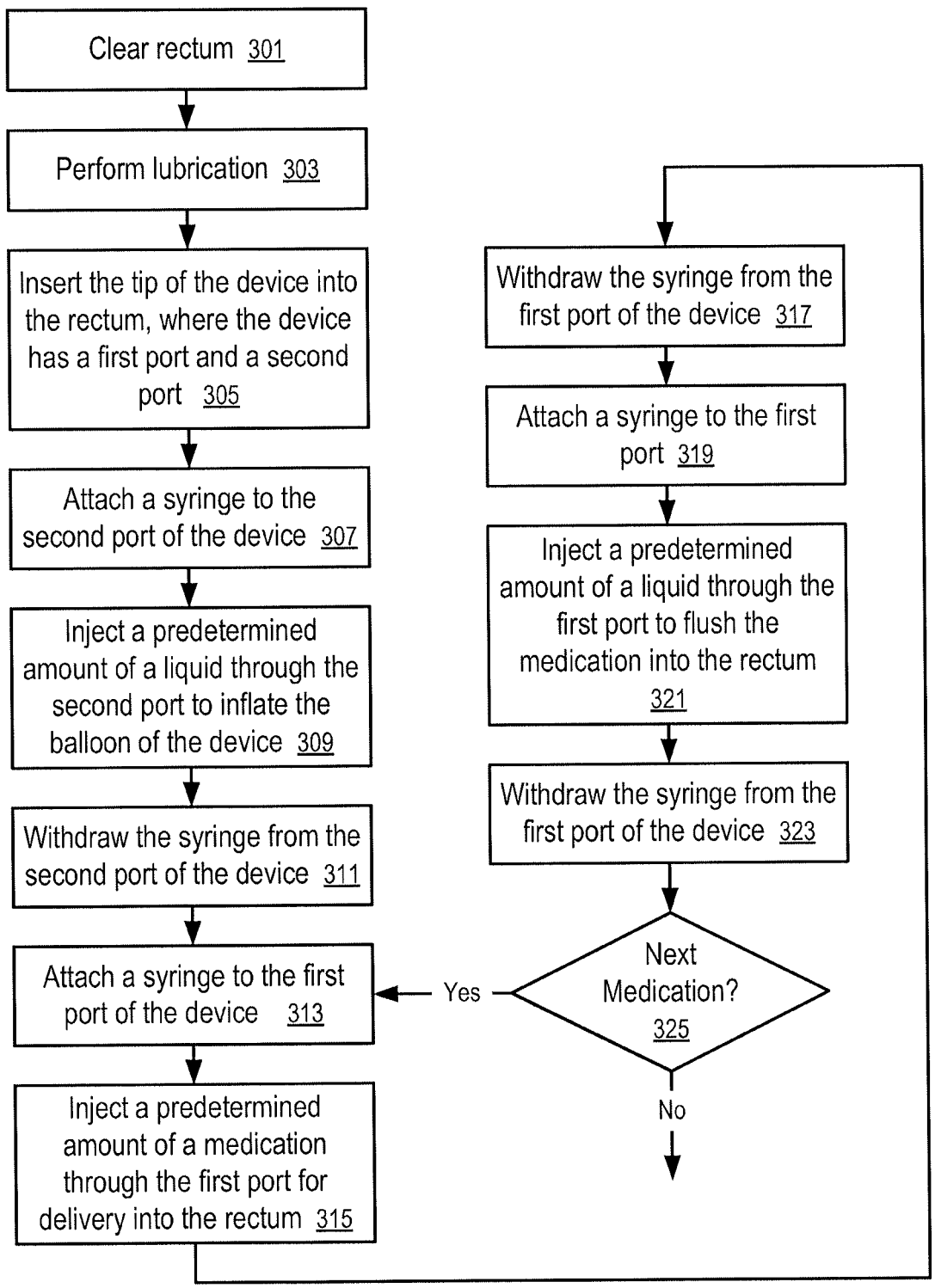
FIG. 6 shows a method to use a device to deliver medication according to one embodiment.

FIG. 6 shows a method to use a device to deliver medication according to one embodiment. In FIG. 6, after the rectum is cleared 301, lubrication of the tip portion of the device is performed 303, using a lubricant, such as water based lubricants. The device has a first port and a second port. After the tip of the device is inserted 305 into the rectum, a syringe can then be attached 307 to the second port of the device to inject 309 a predetermined amount of a liquid through the second port to inflate the balloon of the device.

After the balloon is inflated within the rectum, the syringe can be withdrawn 311 from the second port of the device. The valve in the second port of the device closes to keep the balloon inflated after the syringe is withdrawn.

At a medication time, a syringe is attached 313 to the first port of the device to inject 315 a predetermined amount of medication through the first port for the delivery of medication into the rectum. Then the syringe is withdrawn 317 from the first port of the device.

To flush the medication lumen of the device, a syringe can be attached to the first port 319 to inject a predetermined amount of a liquid, such as water, through the first port. The syringe can then be withdrawn 323 from the first port of the device; and the tip portion of the device can be left inside the rectum for next medication time 325.

Operations 313 through 323 can be performed again at the next medication time without having to move or turn the patient.

Securing the tip portion in the rectum using the balloon and allowing the patient to be in a comfortable position while the medication is applied allow the medication administration be performed over a prolonged period of time. For example, the medication may be applied at a slow continuous rate for a period of time. Alternatively, the medication can be applied periodically (e.g., once every four hours, six hours, twelve hours, etc.)

When the device 100 as illustrated in FIG. 1 is used, the patient does not have to endure the pain and embarrassment of repeated rectal invasion. A patient's current medications can continue to be given easily and effectively when the oral route fails. The device is easy to place, and is easy use by the caregiver. It is easy to replace if it is expelled during defecation. It does not normally cause discomfort and does not stop the passage of stool.

It will be apparent to a skilled artisan that the embodiments described above are exemplary. There could be many alterations made to these examples without departing from the spirit and scope of the invention. For example, different devices could be many different lengths or diameter sizes. The lumen diameters may be different. The devices could be made of many different materials. The devices may or may not have markings to guide insertion depth. The devices may have self closing valves with different technology than that demonstrated. The devices may or may not have balloons. These and many other features may change in different embodiments of the devices.

In the foregoing specification, the disclosure has been provided with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

What is claimed is:

1. A rectal medication administration device comprising:
   a tube comprising a first lumen, a second lumen and a plurality of holes extending from the first lumen through a wall of the tube;
   a balloon proximal to the plurality of holes and having a cavity therein in communication with the second lumen, wherein the balloon is configured to be inflated to hold the tube in place within a patient's rectum;
   a first valved port in communication with the first lumen, wherein the first valved port is configured to open when connected to a first syringe or infusion set to provide medication transmission therethrough and to close when the first syringe or infusion set is withdrawn; and
   a second valved port in communication with the second lumen, wherein the second valved port is configured to open when connected with a second syringe to provide fluid to inflate the balloon and to close when the second syringe is withdrawn;
   wherein the device is configured to be expelled through a rectal sphincter during defecation.

2. The device of claim 1, wherein a distal-most tip of the tube is closed.

3. The device of claim 1, wherein the device is configured such that when the balloon is inflated in the patient's rectum, the plurality of holes are positioned in a distal portion of the patient's rectum.

4. The device of claim 3, wherein the distal portion of the patient's rectum is a distal ⅓ of the patient's rectum.

5. The device of claim 1, wherein an outer diameter of the tube is between 5.5 to 7 millimeters.

6. The device of claim 5, wherein a diameter of the first lumen is 2 millimeters;
   and a diameter of the second lumen is less than 1 millimeter.

7. The device of claim 1, wherein each of the first and second valved ports includes a luer lock connector and valve.

8. The device of claim 1, wherein a diameter of each hole of the plurality of holes is between 1.5 and 2 millimeters, and wherein a spacing between neighboring holes of the plurality of holes is between 4 and 6 millimeters.

9. The device of claim 1, further comprising a marker on the tube configured to indicate a depth of insertion of the tube into the patient's rectum.

10. The device of claim 9, wherein the marker is between 3 and 4.5 inches away from a distal-most tip of the tube.

11. The device of claim 1, wherein the balloon has a diameter of approximately 1 inch when fully inflated.

12. The device of claim 1, wherein the first and second lumens run alongside of one another within the tube.

13. The device of claim 1, wherein the balloon is further configured to be deflated to enable insertion and removal of the device from the patient's rectum.

14. A rectal medication administration device comprising:
   a tube comprising a first lumen, a second lumen and a plurality of holes extending from the first lumen through a wall of the tube;
   a balloon proximal to the plurality of holes and having a cavity therein in communication with the second lumen, wherein the balloon is configured to be inflated to hold the tube in place within a patient's rectum, the balloon having a pliability sufficient to allow the inflated balloon to pass through a rectal sphincter during defecation;
   a first valved port in communication with the first lumen, wherein the first valved port is configured to open when connected to a first syringe or infusion set to provide medication transmission therethrough and to close when the first syringe or infusion set is withdrawn; and
   a second valved port in communication with the second lumen, wherein the second valved port is configured to open when connected with a second syringe to provide fluid to inflate the balloon and to close when the second syringe is withdrawn.

15. The device of claim 14, wherein the device is configured such that when the balloon is inflated in the patient's rectum, the plurality of holes are positioned in a distal portion of the patient's rectum.

16. The device of claim 15, wherein the distal portion of the patient's rectum is a distal ⅓ of the patient's rectum.

17. The device of claim 14, wherein the balloon has a diameter of approximately 1 inch when fully inflated.

18. The device of claim 14, wherein the balloon is further configured to be deflated to enable insertion and removal of the device from the patient's rectum.

* * * * *